(12) United States Patent
Ewers et al.

(10) Patent No.: US 7,955,253 B2
(45) Date of Patent: Jun. 7, 2011

(54) APPARATUS AND METHODS FOR ACHIEVING ENDOLUMINAL ACCESS

(75) Inventors: Richard C. Ewers, Fullerton, CA (US); Boris Reydel, West Caldwell, NJ (US); Eugene G. Chen, Carlsbad, CA (US); Vahid Saadat, Saratoga, CA (US)

(73) Assignee: USGI Medical, Inc., San Clemente, CA (US)

( * ) Notice: Subject to any disclaimer, the term of this patent is extended or adjusted under 35 U.S.C. 154(b) by 1415 days.

(21) Appl. No.: 11/311,999

(22) Filed: Dec. 19, 2005

(65) Prior Publication Data

US 2006/0100480 A1    May 11, 2006

Related U.S. Application Data

(63) Continuation of application No. 10/746,286, filed on Dec. 23, 2003, now abandoned.

(60) Provisional application No. 60/436,518, filed on Dec. 24, 2002.

(51) Int. Cl.
A61B 1/00 (2006.01)
(52) U.S. Cl. .................. 600/114; 600/115; 600/144
(58) Field of Classification Search .................. 600/101, 600/104, 114–116; 606/32–58
See application file for complete search history.

(56) References Cited

U.S. PATENT DOCUMENTS

| | | | |
|---|---|---|---|
| 2,855,934 A | 10/1958 | Daughaday, Jr. | |
| 3,485,237 A | 12/1969 | Bedford | |
| 3,665,928 A | 5/1972 | Del Guercio | |
| 3,683,891 A | 8/1972 | Eskridge et al. | |
| 3,749,085 A | 7/1973 | Wilson et al. | |
| 3,895,637 A | 7/1975 | Choy | |
| 4,066,070 A | 1/1978 | Utsugi | |
| 4,148,307 A | 4/1979 | Utsugi | |
| 4,176,662 A | 12/1979 | Frazer | |
| 4,207,872 A | 6/1980 | Meiri et al. | |
| 4,389,208 A | 6/1983 | LeVeen et al. | |
| 4,577,621 A * | 3/1986 | Patel | 600/114 |
| 4,676,228 A | 6/1987 | Krasner et al. | |
| 4,690,131 A | 9/1987 | Lyddy, Jr. et al. | |
| 4,834,724 A | 5/1989 | Geiss et al. | |
| 4,935,025 A | 6/1990 | Bundy et al. | |
| 5,073,166 A | 12/1991 | Parks et al. | |
| 5,337,733 A * | 8/1994 | Bauerfeind et al. | 600/139 |
| 5,454,364 A * | 10/1995 | Kruger | 600/114 |
| 5,562,601 A | 10/1996 | Takada | |
| 5,624,381 A | 4/1997 | Kieturakis | |
| 5,716,410 A | 2/1998 | Wang et al. | |
| 5,762,069 A | 6/1998 | Kelleher et al. | |
| 5,814,064 A | 9/1998 | Daniel et al. | |

(Continued)

OTHER PUBLICATIONS

Eubanks et al., "35. Flexible Endoscopy of the Lower GI Tract" *Mastery of Endoscopic and Laparoscopic Surgery*, Eubanks, Swantrom, Soper (© 2000) Lippincott Williams & Wilkins Publishers, p. 337.

(Continued)

*Primary Examiner* — Matthew J Kasztejna
(74) *Attorney, Agent, or Firm* — Charles C. Fowler; Levine Bagade Han LLP

(57) ABSTRACT

The present invention provides methods and apparatus for pleating at least a portion of a patient's body lumen, such as the colon. Pleating is achieved via relative motion between an endoscope and a flexible conduit having an engagement element configured to reversibly engage the body lumen.

7 Claims, 15 Drawing Sheets

U.S. PATENT DOCUMENTS

| | | | |
|---|---|---|---|
| 5,984,932 A * | 11/1999 | Yoon | 606/147 |
| 5,989,230 A | 11/1999 | Frassica | |
| 5,993,466 A * | 11/1999 | Yoon | 606/147 |
| 6,007,482 A | 12/1999 | Madni et al. | |
| 6,056,770 A | 5/2000 | Epstein et al. | |
| 6,071,234 A | 6/2000 | Takada | |
| 6,083,216 A | 7/2000 | Fischer, Sr. | |
| 6,102,887 A | 8/2000 | Altman | |
| 6,162,171 A | 12/2000 | Ng et al. | |
| 6,238,412 B1 | 5/2001 | Dubrul et al. | |
| 6,270,515 B1 | 8/2001 | Linden et al. | |
| 6,280,441 B1 | 8/2001 | Ryan | |
| 6,306,081 B1 | 10/2001 | Ishikawa et al. | |
| 6,306,163 B1 | 10/2001 | Fitz | |
| 6,309,346 B1 | 10/2001 | Farhadi | |
| 6,352,503 B1 * | 3/2002 | Matsui et al. | 600/104 |
| 6,379,334 B1 | 4/2002 | Frassica | |
| 6,391,044 B1 | 5/2002 | Yadav et al. | |
| 6,527,753 B2 * | 3/2003 | Sekine et al. | 604/264 |
| 6,544,195 B2 | 4/2003 | Wilson et al. | |
| 6,626,917 B1 | 9/2003 | Craig | |
| 6,716,196 B2 | 4/2004 | Lesh et al. | |
| 6,761,685 B2 * | 7/2004 | Adams et al. | 600/121 |
| 6,800,056 B2 | 10/2004 | Tartaglia et al. | |
| 6,869,393 B2 * | 3/2005 | Butler | 600/114 |
| 2001/0041874 A1 | 11/2001 | Reydel | |
| 2002/0156454 A1 | 10/2002 | Reydel | |
| 2003/0069472 A1 * | 4/2003 | Butler | 600/121 |
| 2004/0077926 A1 * | 4/2004 | Moriyama | 600/101 |
| 2004/0122422 A1 | 6/2004 | Ein-Gal | |
| 2004/0193008 A1 | 9/2004 | Jaffe et al. | |
| 2004/0193009 A1 | 9/2004 | Jaffe et al. | |
| 2005/0020901 A1 | 1/2005 | Belson et al. | |
| 2005/0096502 A1 * | 5/2005 | Khalili | 600/106 |

OTHER PUBLICATIONS

Keymed, "Guide Wires," [Brochure] retrieved from the internet: <<http://www.keymed.co.uk/index.cfm/page/products.index.cfm/id/634/navid/634/parentid/620>> on Dec. 7, 2005. 2 Pages.

* cited by examiner

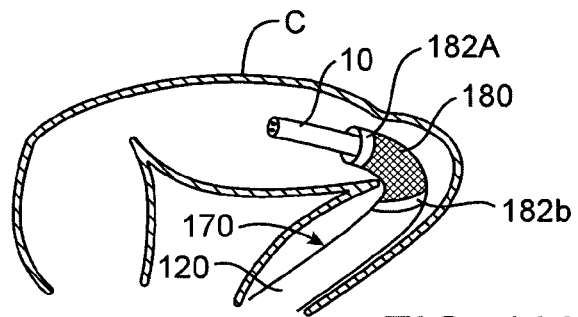
FIG. 11A
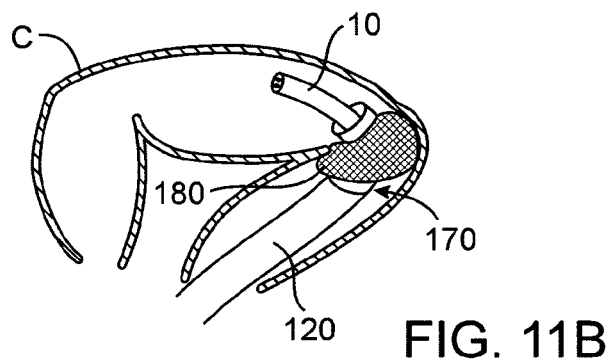
FIG. 11B
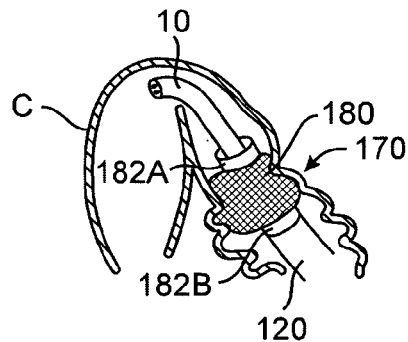
FIG. 11C
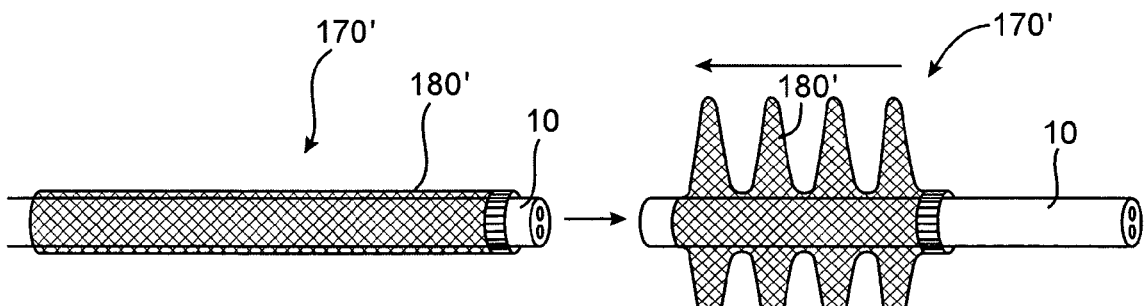
FIG. 12A
FIG. 12B

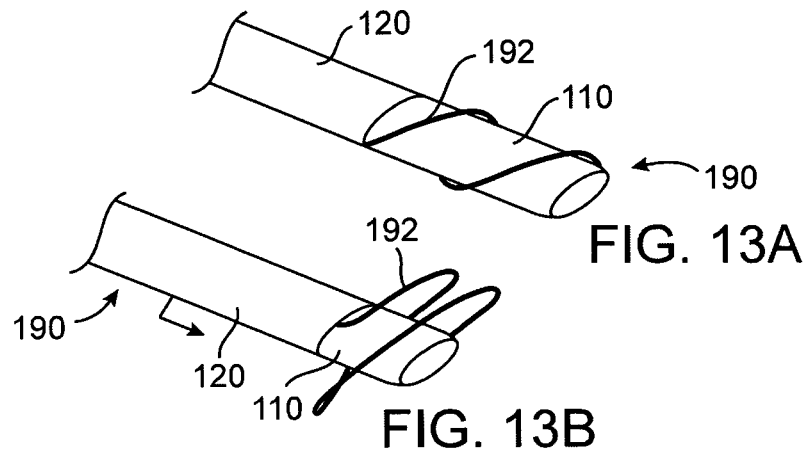
FIG. 13A
FIG. 13B
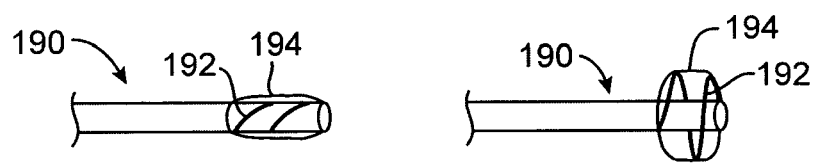
FIG. 13C    FIG. 13D
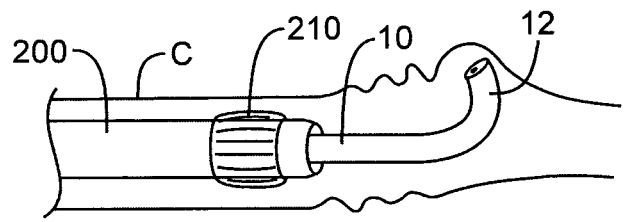
FIG. 14A
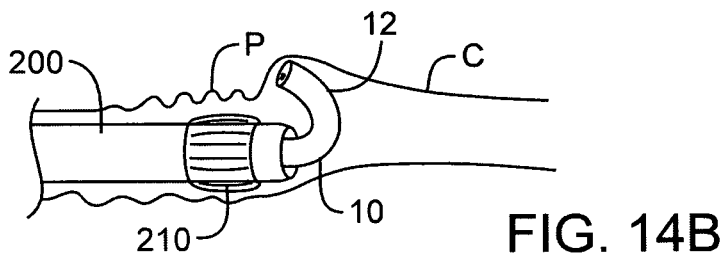
FIG. 14B
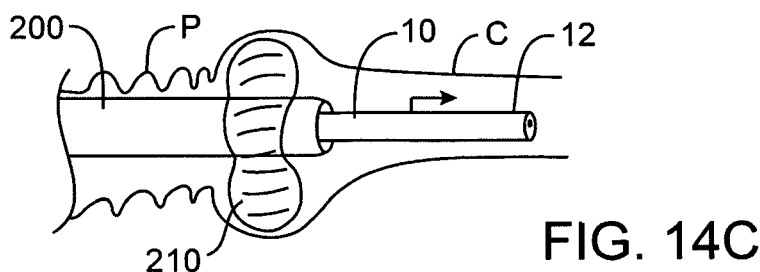
FIG. 14C

APPARATUS AND METHODS FOR ACHIEVING ENDOLUMINAL ACCESS

CROSS-REFERENCES TO RELATED APPLICATIONS

This application is a continuation of U.S. patent application Ser. No. 10/746,286, filed Dec. 23, 2003, which claims benefit of U.S. Provisional Patent Application Ser. No. 60/436,518, filed Dec. 24, 2002, which are incorporated herein by reference in their entirety.

BACKGROUND OF THE INVENTION

1. Field of the Invention

The present invention relates to methods and apparatus for achieving endoluminal access for instruments, e.g. tubular, fiberoptic instruments, such as colonoscopes, gastroscopes, and the like. More particularly, the present invention relates to methods and apparatus for achieving endoluminal access via anatomical pleating.

2. Description of the Background Art

A physician performing a gastrointestinal examination or treatment commonly advances a colonoscope through a patient's anus into the patient's colon. In order to permit full examination of the colon, the colonoscope must be advanced up to the cecum. Advancement may be directed via a steerable distal end portion of the colonoscope. However, at bends in the colon—namely at the sigmoid, and especially at the two colonic flexures—advancement problems regularly occur, including a risk of injury, pain to the patient, cramp-like contractions of the colon, and even an inability to further advance the colonoscope.

Such problems stem from the fact that the colon is soft and weakly adhered to the abdomen. After a first deflection of the colonoscope, a principal direction of force by which the colonoscope is advanced no longer points towards the distal end of the colonoscope, but rather points towards the readily yielding wall of the colon. Force application is unpleasant to the patient and precludes access to the cecum in about 10% to 15% of all cases.

The concept of pleating or "accordionizing" the colon to facilitate advancement of the colonoscope is described by Eubanks et al. in Mastery of Endoscopic and Laparascopic Surgery, Eubanks, Swantrom, Soper, pg. 337, 2000, Lippincott Williams & Wilkins.

"If the colon were a simple noncompliant tube without redundancy or irregularity, colonoscopic intubation would be a rather simple endeavor of advancing the scope while following the tip. Occasionally, especially if there has been a prior sigmoid resection, colonoscopy may be no more demanding than simple scope advancement. However straight advancement usually promotes the development of loops, stretching the colon. When progression of the scope is not impeded by severe tip deflection, the colon can be encouraged to accordionize along the length of the scope. This is most likely to occur if the scope is repeatedly advanced and withdrawn. In some areas, particularly distally, this is most effective if it is performed with small rapid strokes, referred to as dithering the scope. Elsewhere, such as the transverse colon, this maneuver is performed with long, gentle strokes of 30 to 50 cm."

FIGS. 1-3 describe Prior Art methods of accomplishing such accordionization or pleating, as described by Eubanks et al. In FIG. 1, elongation intubation of colon C through anus A is described using colonoscope 10 having steerable deflection tip 12. In FIG. 1A, scope 10 is advanced into proximal sigmoid S. Deflection tip 12 then is turned into the distal descending colon DC, as in FIG. 1B. In FIG. 1C, sigmoid S is accordionized onto scope 10 via simultaneous clockwise torqueing, shaft withdrawal and flattening of deflection tip 12. Further distal advancement of scope 10 then is achievable without causing pain to the patient, etc.

FIG. 2 describe intubation via looping. In FIG. 2A, scope 10 is inserted into sigmoid S with counterclockwise torqueing during scope advancement. In FIG. 2B, the broad loop in the sigmoid flattens the sigmoid-descending colon junction. Subsequent clockwise rotation of scope 10 with concurrent withdrawal accordionizes sigmoid S onto the scope.

FIG. 3 describe intubation of ascending colon AC. In FIG. 3A, scope 10 has a view of the ascending colon with sharp angulation in the right colic flexure F. In FIG. 3B, transverse colon TC is elevated into the upper abdomen via clockwise torqueing and withdrawal of scope 10. As seen in FIG. 3C, scope 10 is then advanced via clockwise torqueing of the scope, flattening of deflection tip 12 and evacuation of air from the distended colon C, thereby accordionizing the colon onto the scope. Complete intubation of cecum Ce then is achieved by further advancing scope 10, as in FIG. 3D.

According to Eubanks et al., accordionization most consistently enables examination of the greatest length of colon with the least amount of scope. In contrast to techniques where the scope is advanced up into the colon, accordionization should be viewed as bringing the colon down over the scope.

"This technique employs simultaneous application of both dithering and torqueing. While the shaft is being advanced approximately 6 to 10 cm, a small amount of counterclockwise torque of about 45 to 60 degrees is applied. The process is reversed by applying clockwise torque and simultaneous withdrawal of the scope for the same length. This cycle is repeated in a rhythmic manner at a rate of about one cycle per second, but without advancement of the shaft. It is useful to hold the shaft of the scope close to the anus to avoid over-advancing. Although the first few dithering/torquing cycles may appear to accomplish little, by rhythmically continuing this motion, the cumulative effect is to pleat a short segment of sigmoid colon onto the scope. As one acquires experience with this technique, it soon becomes apparent that the cyclic rhythm, amount of torque, degree of tip deflection, and shaft advancement distance are all variables that can by altered to achieve maximum effect. If this technique is successful, the descending colon can be readily intubated as far as the splenicflexure by applying clockwise torque during shaft advancement with minimal deflection of the tip. With this approach, the endoscopist is attempting to straighten the colon as he or she progresses, rather than intentionally creating a loop that has to be removed later. Several principles should be kept in mind when this technique is performed:

1. This method should be started early in the process of intubation in the rectosigmoid to minimize the deflection angle.
2. It is not always necessary to see the entire lumen, but one should avoid pushing directly into the colonic wall.
3. The endoscopist should resist the temptation to advance the scope as soon as the lumen is seen, and should continue with this process to maximize the accordionization of the entire sigmoid colon.
4. Excessive gas insufflation is a deterrent to accordionization.

5. If this technique is not successful, one can proceed with intentional looping."

As will be apparent, the accordionization technique described by Eubanks et al. requires significant skill and experience on the part of the endoscopist in order to be successful. Furthermore, many variables must be taken into account in order to properly accordionize the colon, including cyclic rhythm, amount of torque, degree of tip deflection, and shaft advancement distance. It is expected that these limitations will hamper broad acceptance of accordionization techniques.

In view of the aforementioned limitations, it would be desirable to provide methods and apparatus for pleating the colon that require less skill and experience on the part of the endoscopist.

It also would be desirable to provide methods and apparatus that simplify and expedite pleating.

BRIEF SUMMARY OF THE INVENTION

In view of the foregoing, it is an object of the present invention to provide methods and apparatus for pleating the colon that require less skill and experience on the part of the endoscopist.

It is another object of the present invention to provide methods and apparatus that simplify and expedite pleating.

These and other objects of the present invention are accomplished by providing apparatus that facilitates formation and retention of colonic pleats, thereby allowing physicians to use the scope as a tool for diagnosis and therapy, rather than as an access tool. The apparatus engages a proximal portion of the lumen to be intubated, and withdraws the lumen proximally over a relatively stationary endoscope or other device. This shortens an elongated section of luminal anatomy by compressing it in an accordion-like fashion over the endoscope or other device.

In a first embodiment, an endoscope is partially advanced with an external engagement sheath. The sheath then is activated to engage the lumen wall. Once engaged, the lumen is pulled proximally by withdrawing or rotating the sheath. In an alternative embodiment, the scope is extended distally of the external sheath to "hook" tissue with its deflectable tip. The scope then is withdrawn towards the sheath, forming a pleat that is pulled back over the sheath. Once a pleat has been formed, an engagement member is activated on the sheath to retain the pleat.

In yet another embodiment, engagement catheters are provided that may be advanced through the scope's working channel. The engagement catheters are extended beyond the scope to engage tissue and withdraw it towards the scope. The engagement catheters optionally may be used in conjunction with an external engagement sheath to initiate, position, and/or capture a pleat. Single anchoring/engagement members may be used, a plurality of engagement members may be used, a continuum of engagement members may be used, multiple sheaths may be used, etc.

Pleating apparatus and methods of the present invention may be utilized to gain full access into a human colon. In contrast to known colonoscopic maneuvering techniques to shorten/straighten the colon and aid in intubation, the present invention provides separate pleating apparatus that may be used in conjunction with the endoscope to replace or reduce difficult prior art scope maneuvering techniques.

Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 11A-11C are side views, partially in section, illustrating a method of pleating the colon with expandable mesh apparatus in accordance with the present invention;

FIGS. 12A and 12B are side views of an alternative embodiment of the apparatus of FIG. 11 comprising a multi-humped expandable mesh, shown collapsed and expanded;

FIGS. 13A-13D are isometric and side views of an alternative embodiment of oversheath pleating apparatus of the present invention comprising an expandable helix;

FIGS. 14A-14C illustrate a method of pleating the colon with a pleat capture sheath of the present invention used in conjunction with a colonoscope;

DETAILED DESCRIPTION OF THE INVENTION

The present invention relates to methods and apparatus for achieving endoluminal access for instruments, e.g. tubular, fiberoptic instruments, such as colonoscopes, gastroscopes, and the like. More particularly, the present invention relates to methods and apparatus for achieving endoluminal access via anatomical pleating.

One aspect of the invention comprises a pleating sheath that is advanceable over a colonoscope. The sheath, which preferably is fabricated from an extrusion of plastic material, is placed over the scope prior to use. Rounding off a leading edge or overmolding of the sheath may provide the sheath with a soft tip of foam or elastomer that acts as an atraumatic tip. Preferably, a metal spring coil is embedded in the wall of the sheath to provide flexibility in combination with kink-resistance. Alternatively, the sheath may be fabricated with a braided component embedded in the wall. This too allows good flexibility while maintaining strength.

The sheath may be configured to minimize friction between itself and the colonoscope. This may be achieved by a variety of techniques, for example, the sheath may have internal ridges or nubs to reduce surface contact area, roller wheels or ball bearings may be provided in the wall to create rolling friction instead of sliding friction, or preferably a hydrophilic coating may be applied to the sheath's inner surface. The coating is activated by wetting with, e.g., water or saline, and significantly reduces the coefficient of friction between the scope and the sheath's internal surface.

In use, the colonoscope preferably is advanced into the colon to a desired or achievable depth. Then, the pleating sheath preferably is back loaded up the scope or is introduced simultaneously with the scope. An anchoring feature preferably is provided at the tip of the sheath to engage the colon wall. The sheath then is withdrawn while the scope is held in place or further advanced. Withdrawal of the activated sheath pulls the colon proximally. The sheath-engaged colon pleats along the scope towards the anus. This shortens the colon by taking its stretched-out natural length and "bunching up" a portion of it.

Figure 1A:
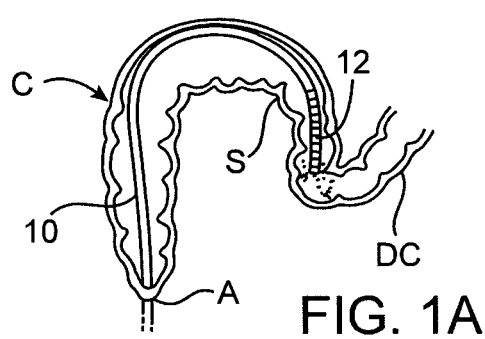
FIGS. 1A-1C are side views, partially in section, illustrating a prior art method of intubating and accordionizing the colon via elongation.
Figure 1B:
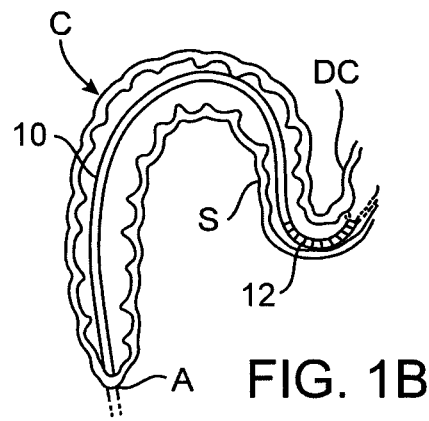
Figure 1C:
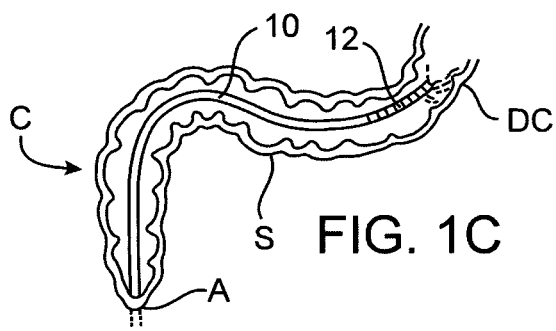
Figure 2A:
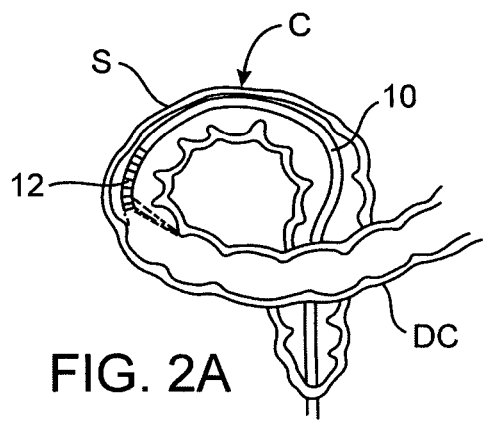
FIGS. 2A-2C are side views, partially in section, illustrating a prior art method of intubating and accordionizing the colon via looping.
Figure 2C:
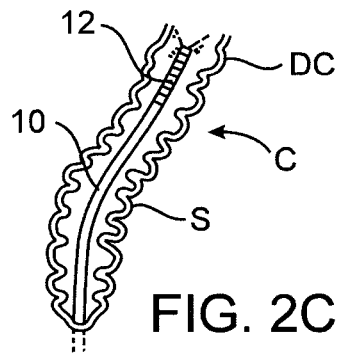
Figure 2B:
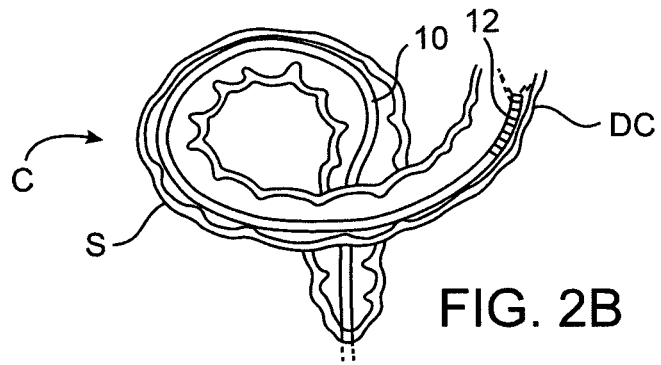
Figures 3A, 3B:
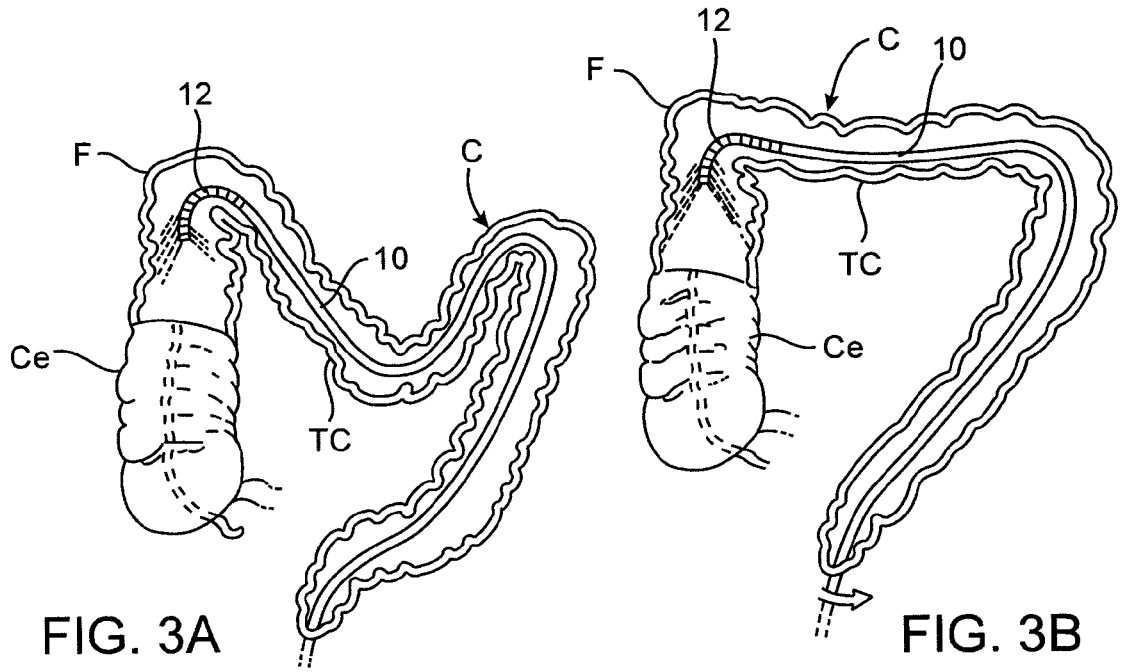
FIGS. 3A-3D are side views, partially in section, illustrating a prior art method of intubating and accordionizing the ascending colon.
Figures 3C, 3D:
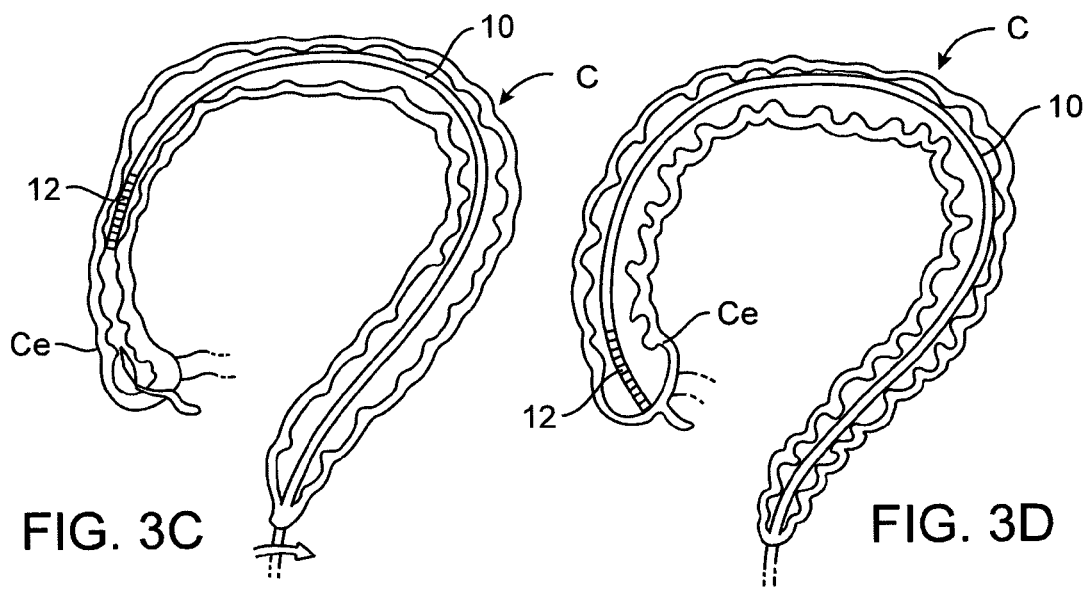
Figure 4A:
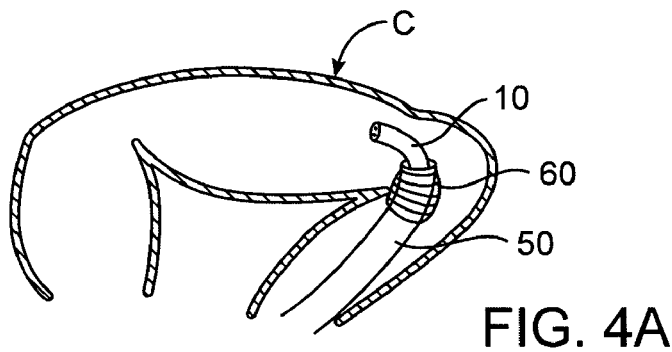
FIGS. 4A-4C are side views, partially in section, illustrating a method of intubating and pleating the colon with a first embodiment of balloon apparatus of the present invention.
Figure 4B:
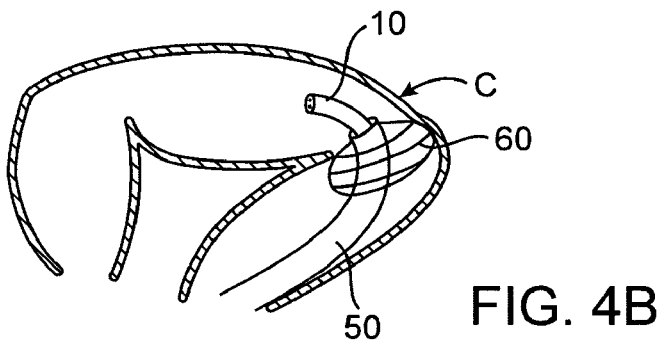
Figure 4C:
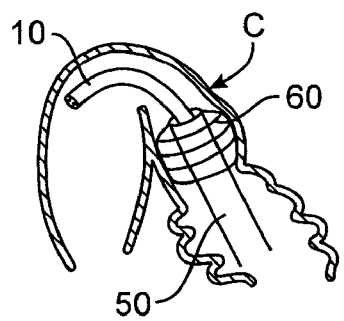
Figure 5:
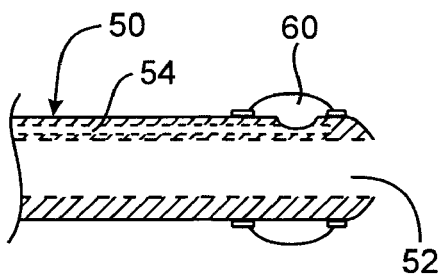
FIG. 5 is a side-sectional view of the apparatus of FIG. 4.
Figure 6:
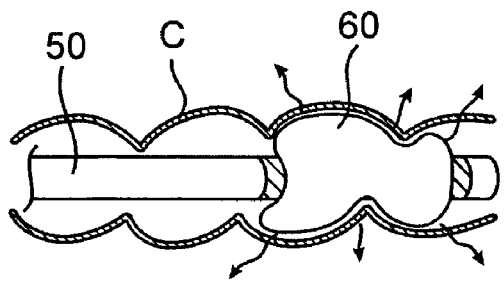
FIG. 6 is a side view, partially in section, illustrating the conformable nature of the apparatus of FIG. 4.

With reference to FIGS. 4-6, a pleating sheath embodiment is described comprising an engagement member having a distensible balloon. In FIG. 4A, pleating sheath 50 is shown advanced over scope 10 to a bend within a patient's colon C. In FIG. 4B, distensible balloon 60 of sheath 50 is inflated to releasably engage the patient's colon in the vicinity of the bend. With colon C engaged, sheath 50 is retracted relative to scope 10, thereby pleating the colon over the scope and facilitating further advancement of the scope, as seen in FIG. 4C. Balloon 60 then may be deflated to disengage sheath 50 from colon C, and the sheath may be further translated relative to scope 10. Balloon 60 may be re-inflated, as desired, to engage the colon at additional locations, for example, to facilitate additional pleating.

FIG. 5 illustrates lumen 52 of sheath 50, which is sized for advancement over scope 10, as well as inflation lumen 54, which facilitates inflation and deflation of balloon 60, e.g., via a standard syringe coupled to a proximal region of the sheath (not shown). The physician inflates the balloon by injecting a prescribed amount of liquid or gas via the syringe. As seen in FIG. 6, distensible balloon 60 has the advantage of achieving a minimal collapsed profile to aid in easy insertion, and also complies with the anatomy wherever it is inflated. The surface of said balloon optionally may have a texture to aid in engaging the wall of the colon.

Figure 7:
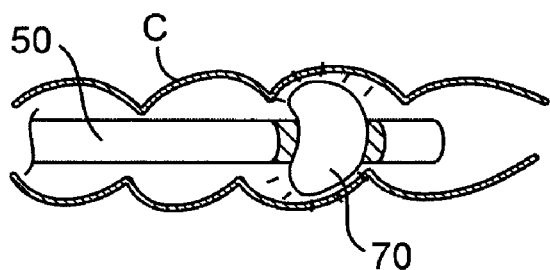
FIG. 7 is a side view, partially in section, illustrating pleating via an alternative, non-conforming embodiment of the balloon apparatus of FIG. 4.

As seen in FIG. 7, a non-distensible balloon alternatively may be provided. Non-distensible balloon 70 advantageously may be preformed into a desired shape. For example, the balloon may be formed to take on the inflated shape of a cone or "barbed" structure that preferentially engages the colon wall upon withdrawal. It also may have a maximum expansion size that could not be overridden by excessive inflation volume.

Figure 8A:
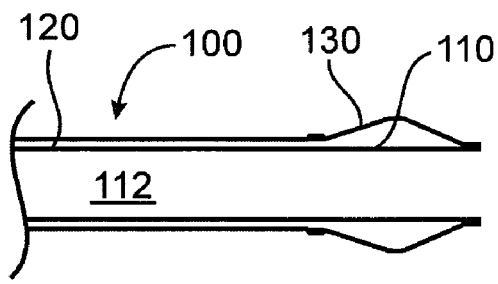
FIGS. 8A and 8B are side-sectional views of another embodiment of apparatus in accordance with the present invention comprising expandable spines, shown, respectively, in a collapsed configuration and in an expanded configuration.
Figure 8B:
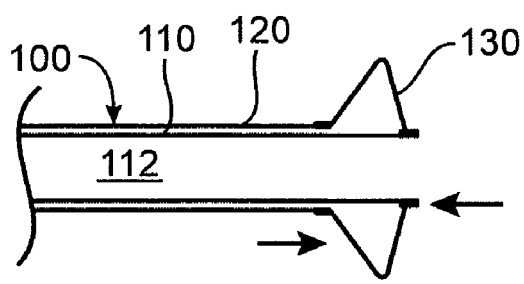

Similar to the balloons described hereinabove, mechanical structures may be used to form the expanding anchor/engagement member. For example, as seen in FIG. 8, concentric sheaths may be provided. Apparatus 100 comprises concentric, thin-walled inner sheath 110 and outer sheath 120. Inner sheath 110 extends slightly distal of outer sheath 120, and comprises inner lumen 112 configured for advancement over scope 10. Spines 130, which may comprise slits formed in outer sheath 120 and/or may, for example, comprise plastic, elastomeric, or metallic spines, connect the tip of inner sheath 110 with the tip of outer sheath 120. Relative translational motion between the two sheaths approximates the connected tips and causes the spines to "elbow out" or expand from the collapsed delivery profile of FIG. 8A to the expanded engagement profile of FIG. 8B.

This relative motion may be achieved with a handle/slider mechanism, per se known, that the user operates to expand or contract the anchoring spines as desired. Alternatively, the mechanism for forming the "elbowed out" spines may use temperature-activated memory metal or plastic, in which flushing with a particular temperature liquid causes the spines to take on a desired profile. Electrical heating may also be used.

Figure 9A:
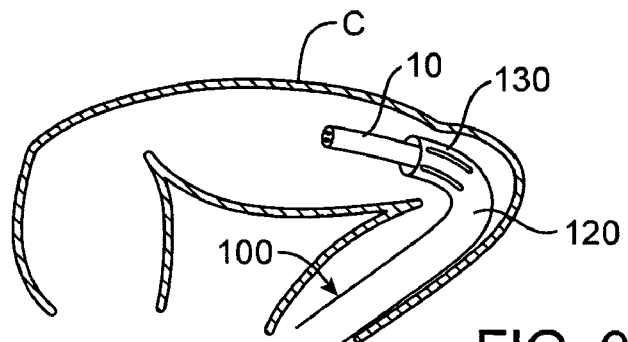
FIGS. 9A-9C are side views, partially in section, illustrating a method of pleating the colon with the apparatus of FIG. 8.
Figure 9B:
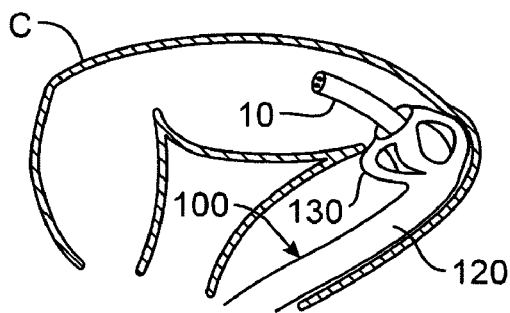
Figure 9C:
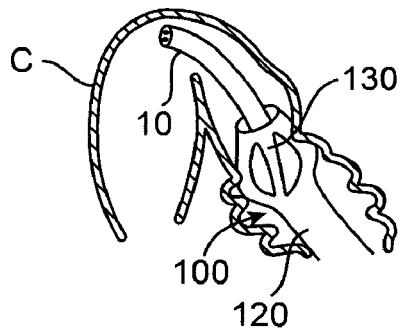

With reference to FIG. 9, a method of using apparatus 100 to pleat colon C is described. In FIG. 9A, apparatus 100 is advanced over scope 10 to a tortuous bend in the colon. Outer sheath 120 is then advanced relative to inner sheath 110, which causes spines 130 to expand outward and reversibly engage colon C, as in FIG. 9B. In FIG. 9C, apparatus 100 is withdrawn relative to scope 10, thereby pleating the colon over the scope and facilitating further distal advancement of the scope. Outer sheath 120 may then be retracted relative to inner sheath 110 to disengage spines 130 from colon C. This cycle of relative motion between scope 10, inner sheath 110 and outer sheath 120 may be repeated as desired at additional distal locations within the colon to further pleat the colon.

Figure 10A:
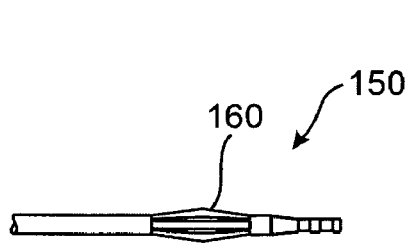
FIGS. 10A and 10B, respectively, are side and isometric views of alternative expandable spine apparatus shown collapsed and expanded.
Figure 10B:
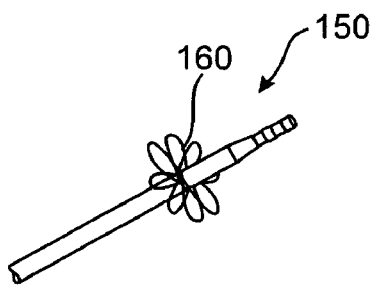

With reference to FIG. 10, a particularly atraumatic expanded spine structure is described. Apparatus 150 comprises spines 160 that not only "elbow out," they also "loop out" simultaneously to create a smooth edged expanded profile. FIG. 9A illustrates the collapsed configuration, while FIG. 9B illustrates the expanded configuration.

Referring now to FIG. 11, expandable, tubular-braid like material also may be used. Braided mesh 180 of apparatus 170 is extremely porous and compliant, yet exceptionally strong due to the composition of numerous interlaced fibrous elements. Braid 180 is made from individual monofilament elements combined in an opposing helical pattern. The nature of the braided tubular structure allows it to have two diameter states. Axial tension of opposing ends of the braid causes it to elongate and reduce in diameter, as in FIG. 11A. Axial compression causes the braid to reduce in length while simultaneously expanding in diameter, as in FIGS. 11B and 11C. A disk-like anchor is made by forming two ends of a short length of braid into small diameter collars 182A and 182B. This may be accomplished by heat forming the mesh into continuous, diametrically fixed bushings that transition into the braid tube. Alternatively, the braid may be glued, overmolded, soldered, welded onto separate bushings. These bushings are then connected to, e.g., co-axial sheaths 110 and 120 described above. Bringing the sheath ends in closer proximity causes braided spines 180 to expand outwardly into the anchoring disk of FIGS. 11B and 11C.

In FIG. 11A, apparatus 170 is coaxially advanced over scope 10 to a bend in colon C. Mesh 180 is then expanded to engage the colon, as in FIG. 11B. Next, apparatus 170 is retracted relative to scope 10, as in FIG. 11C, thereby pleating the colon over the scope and facilitating further distal advancement of the scope. Mesh 180 is then collapsed, and the pleating technique may be repeated, as needed.

With reference to FIG. 12, an alternative embodiment of apparatus 170 is described. Apparatus 170' comprises 'accordion' mesh 180' that forms multiple humps upon expansion, as seen in FIG. 12B, but that may be reduced for coaxially translation about scope 10, as in FIG. 12A. It is expected that the multiple humps of accordion mesh 170' will facilitate pleating of the colon by contacting the colon over an increased surface area.

Referring now to FIG. 13, much like the expanding spines and braid meshes described hereinabove, resilient helix 192 of apparatus 190 may be drawn down to a low profile by attaching the ends of the helix to concentrically-disposed inner sheath 110 and outer sheath 120. Bringing the tube ends together expands helix 192, as in FIG. 13B, while pulling them apart collapses the helix, as in FIG. 13A. As seen FIGS. 13C and 13D, optional elastomeric jacket 194 may be placed over helix 192 in order to spread the contact area over a wider location than just the helix, thereby making the helix less traumatic. The spiral nature of expanding helix 192 also promotes some rotational motion of the tip, like an auger, which may help induce colon engagement or proximal motion of the colon. Alternatively, the helix may be made of temperature-activated memory metal or plastic, in which expansion of the helix is activated by exposure to a liquid of a predetermined temperature or electrical heating. Apparatus 190, as well as the other mechanically expanding structures described hereinabove, may be used like the balloon embodiments to engage the colon wall, after which proximal motion of the sheath causes pleating.

Apparatus of the present invention described with respect to FIGS. 4-13 illustrate use of an activated pleating sheath to actively pull back the colon wall. With reference to FIG. 14, pleat capture sheath 200 is described, wherein colon C is pleated via engagement anchor 210, which is used to capture pleat P formed by a hooking maneuver conducted with deflection tip 12 of scope 10. In FIG. 14A, scope 10 is advanced beyond a distal end of apparatus 200, deflection tip 12 is steered into a hook shape, engaged to the colon wall, and then drawn back. The colon thereby forms pleat P over apparatus 200, as seen in FIG. 14B. As seen in FIG. 14C, engagement anchor 210 then may be activated to engage colon C and create a physical stop point so that pleat P cannot spontaneously slide forward on its own. Forming the pleat with scope 10 and capturing it with apparatus 200 may be repeated multiple times until the desired section of colon is available. Engagement member 210 of apparatus 200 may employ any of the engagement structures described and illustrated previously, as well others, per se known. In FIG. 14, engagement member 210 illustratively comprises an expandable balloon.

Figure 15A:
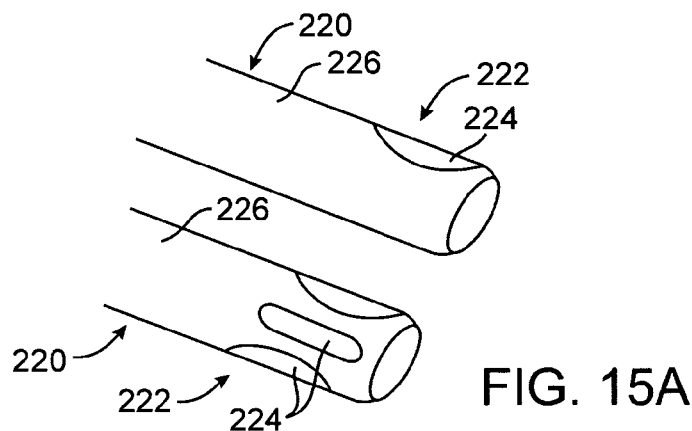
FIGS. 15A-15C are, respectively, isometric, side-sectional, and cross-sectional views of suction pleating apparatus of the present invention.
Figure 15B:
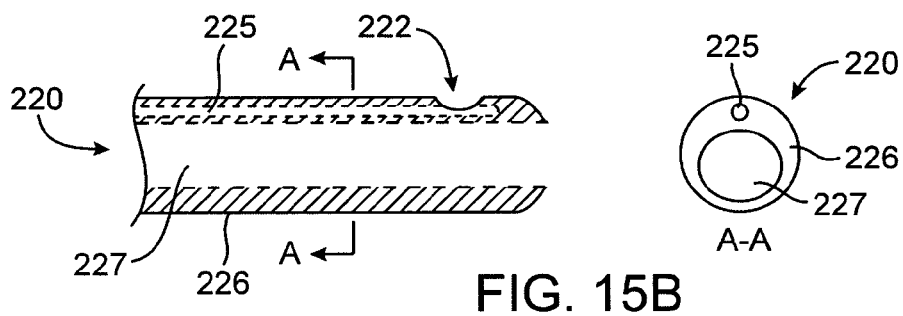
Figure 15C:
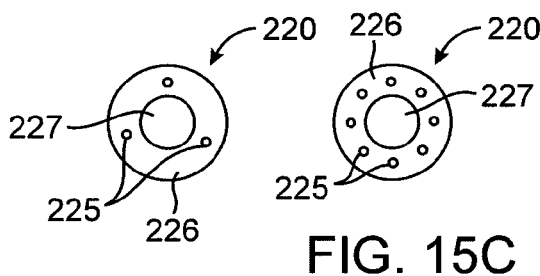

Referring now to FIG. 15, suction is used commonly in the GI tract to bring an endoscope into contact with mucosa. Accordingly, as seen in FIG. 15A, apparatus 220 may comprise suction anchor 222 having one or more suction ports 224 disposed on a distal region of sheath 226, for example, to pleat the colon or capture pleats formed by scope 10. Scope 10 may be translated within lumen 227 of sheath 226, as seen in FIG. 15B. Preferably, one or more evacuation lumens 225 run through the sheath and attach externally to a vacuum source (see FIG. 16). FIG. 15C illustrate exemplary alternative cross-sections of sheath 226 along section line A-A of FIG. 15B. Additional evacuation lumens 225 may be provided, as needed, to couple additional suction ports 224 of suction anchor 222 to the vacuum source. Suction-based engagement may replace any of the expandable anchors shown and described above.

Figure 16:
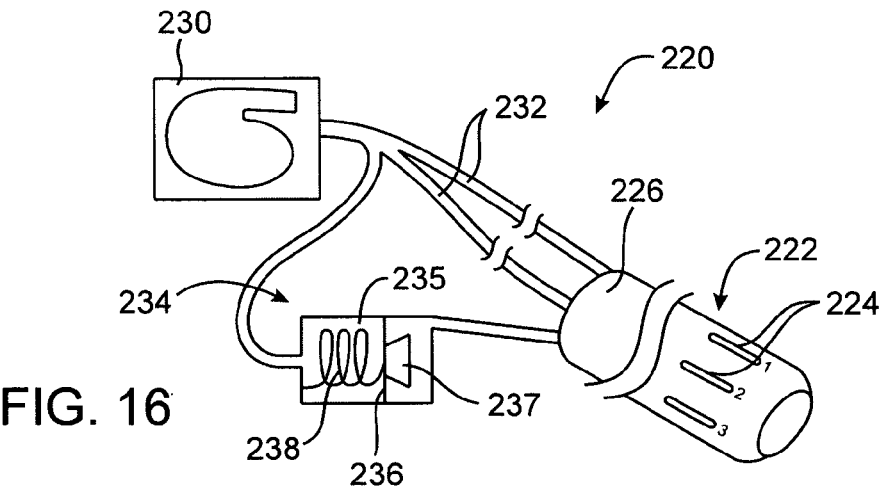
FIG. 16 is a schematic view of an illustrative vacuum source and shut-off valve for use with the apparatus of FIG. 15.

When numerous suction ports 224 are provided, a system of vacuum shut off valves may be used to block the continuation of suction through ports not in contact with tissue. For example, as shown in FIG. 16, each port 224 may be coupled to vacuum source 230 via a vacuum line 232 having a valve 234. Each valve may comprise chamber 235 having aperture 236 through which cork 237 may be removably disposed to prevent flow therethrough. Cork 237 may be coupled to compression spring 238 that biases the cork from occluding aperture 236 when its associated port 224 is in contact with tissue. When associated suction port 224 is not in contact with tissue, vacuum source 230 aspirates cork 237 against the biasing force of compression spring 238 to occlude aperture 236, thereby decoupling vacuum source 230 from the non-contacting port 224. This prevents apparatus 220 from spontaneously adhering to different places after an initial acceptable anchoring occurs. Also, this feature prevents a continual evacuation of insufflation gas after anchoring is achieved. Generally, a quantity of gas pressure is desired in the colon to help tent it so that it is more easily accessed and visualized.

Figure 17A:
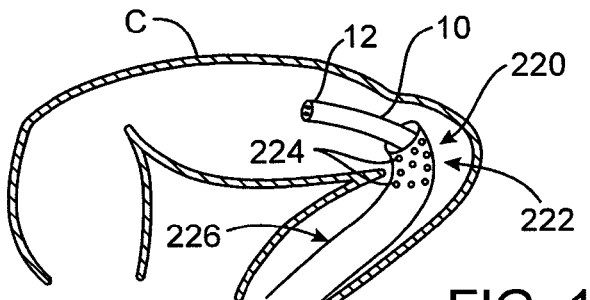
FIGS. 17A-17C are side views, partially in section, illustrating a method of pleating the colon utilizing the apparatus of FIG. 15 as an oversheath pleater.
Figure 17B:
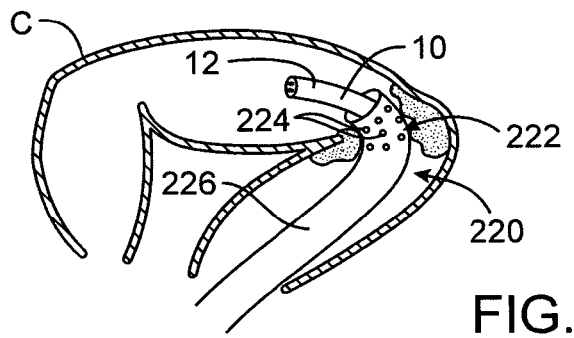
Figure 17C:
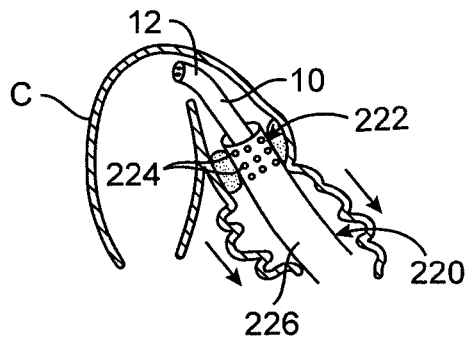

With reference to FIG. 17, a method of using apparatus 220 as a pleating oversheath to pleat the colon is described. As will be apparent, apparatus 220 alternatively may be used to capture pleats formed via deflection tip 12 of scope 10. In FIG. 17A, apparatus 220 is translationally advanced over scope 10. Activation of vacuum source 230 causes distal vacuum ports 224 of vacuum anchor 222 to attach to mucosa along the wall of colon C, as in FIG. 17B. As seen in FIG. 17C, vacuum-anchored sheath 226 then is withdrawn relative to scope 10, thereby pleating the colon as described previously.

Advantageously, vacuum anchor 222 provides apparatus 220 with a small profile, even while engaging tissue. A degree of anchoring achievable with apparatus 220 may be specified, for example, by controlling the size of vacuum ports 224, the strength of suction applied by vacuum source 230, and inclusion of safety vents. An optional release mechanism (not shown) may also be provided, whereby suction anchor 222 releases colon C when sheath 226 is retracted with sufficient force.

Suction anchor 222 may have numerous configurations. For example, suction port(s) 224 may be configured as a single point, an elongated window, or multiple windows. Furthermore, port(s) 224 may be located at a specific position along the wall of sheath 226, or may be distributed about the diameter or circumference.

Figure 18:
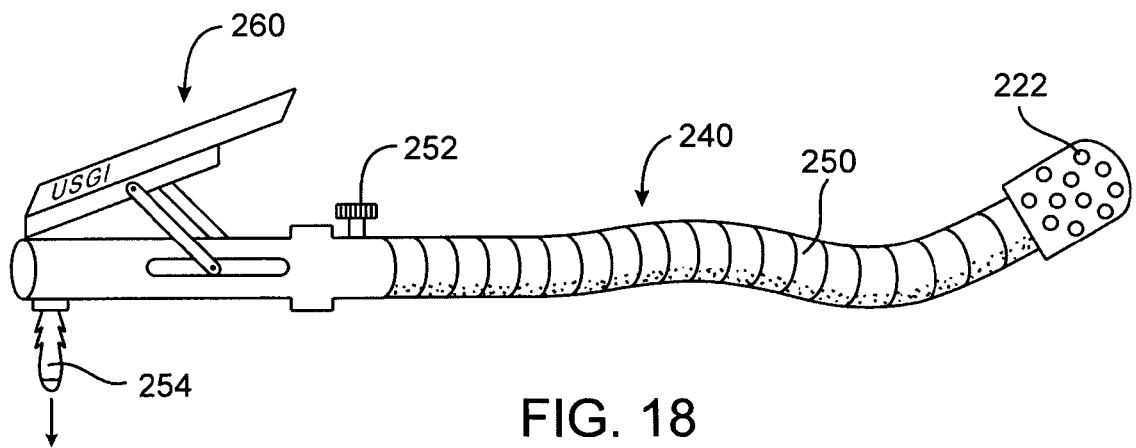
FIG. 18 is a schematic view of alternative suction pleating apparatus comprising a shape-lockable overtube.
Figure 19A:
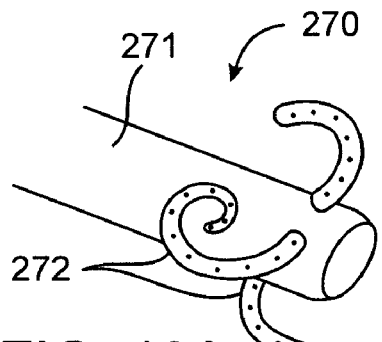
FIGS. 19A-19D are isometric views of further alternative suction pleating apparatus comprising various extendable anchors.
Figure 19B:
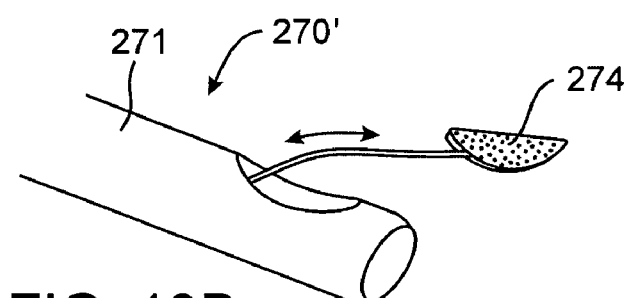
Figure 19C:
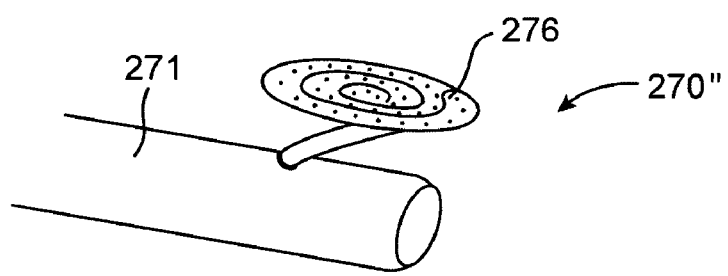
Figure 19D:
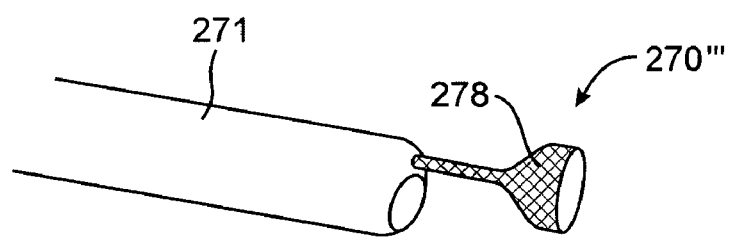

Referring now to FIG. 18, alternative suction anchoring apparatus in accordance with the present invention is described. Apparatus 240 comprises shape-lockable overtube 250 having suction anchor 222 disposed on a distal end of the overtube. Apparatus 250 further comprises actuation handle 260 disposed at a proximal end of overtube 250 for reversibly transitioning the overtube from a flexible configuration to a substantially rigid configuration while the overtube is disposed in a desired arrangement. Shape-lockable overtubes are described in greater detail in Applicant's co-pending U.S. patent application Ser. No. 10/281,462, filed Oct. 25, 2002, which is incorporated herein by reference in its entirety. Suction activation valve 252, as well as suction conduit 254 for attaching to vacuum source 230, is also coupled to handle 260.

Apparatus 240 may be used to pleat a patient's colon in a manner similar to that described for apparatus 220 in FIG. 17. Handle 260 may then be actuated to reversibly rigidize overtube 250 and maintain the colon in the pleated configuration. Scope 10 may be advanced through handle 260 and overtube 250.

Referring to FIG. 19, to enhance engagement of suction ports to the colon wall, the suction ports may be configured to extend beyond the sheath. Such deployable ports advantageously facilitate contacting of the colon wall over a larger surface area, thereby enhancing holding force. Various low profile or deployable appendages may be utilized. In FIG. 19A, apparatus 270 comprises a plurality of ported coils 272 that may be extended out of sheath 271 to "find" and engage the colon wall. In FIG. 19B, apparatus 270' comprises thin, elongated suction pad 274 that extends from sheath 271. In FIG. 19C, apparatus 270" comprises pre-shaped, ported tube 276 that may be advanced out of sheath 271 to form a helical suction pad. In FIG. 19D, apparatus 270'" comprises elastomerically coated mesh hose or braid 278 that may be extended from sheath 271 to form a large-surface-area suction funnel. Additional extendable suction anchors will be apparent to those of skill in the art.

Figure 20:
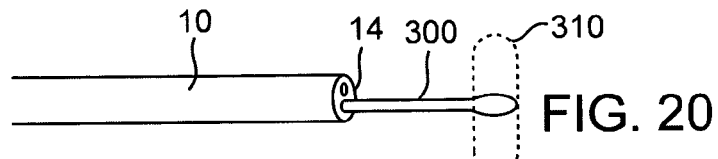
FIG. 20 is a schematic view of pleating apparatus of the present invention configured for delivery through the working channel of a colonoscope.
Figure 21A:
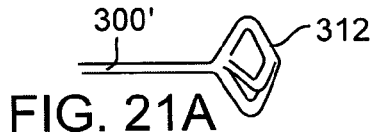
FIGS. 21A-21D are schematic views of various alternative engagement tips for the apparatus of FIG. 20.
Figure 21B:
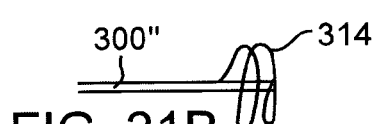
Figure 21D:
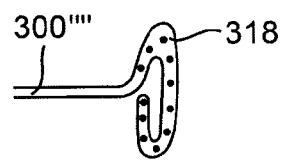
Figure 21C:

Apparatus and methods of the present invention described thus far comprise apparatus configured for advancement over scope 10 in order to pleat the colon. An alternative method for engaging the colon and creating pleats employs tools disposed through the working channel of the scope. With reference to FIG. 20, catheter 300 with expanding tip 310 may be advanced through working channel 14 beyond the distal tip of scope 10, and then activated to engage the colon distal of the scope. Withdrawal of the catheter relative to the scope pulls the colon back towards the scope tip, thereby causing a pleat to form on the scope. Expanding tip 310 may comprise any of the expanding structures described previously, including suction.

FIG. 21 illustrate various embodiments of catheter 300. In FIG. 21A, expandable tip 310 of catheter 300' comprises Malcot 312. In FIG. 21B, tip 310 of catheter 300" comprises helix 314. Catheter 300'" of FIG. 21C comprises hook 316, while catheter 300"" of FIG. 21D comprises pre-shaped suction tube 318. Additional engagement tip will be apparent to those of skill in the art.

Figure 22A:
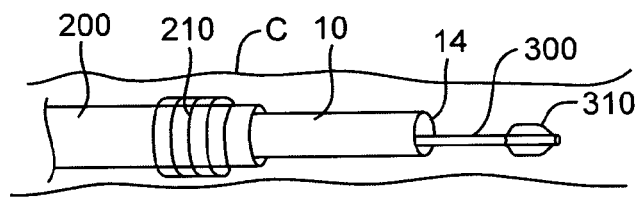
FIGS. 22A-22D are side views, partially in section, illustrating a method of using the through-scope pleating apparatus of FIG. 20 in conjunction with the pleat capture apparatus of FIG. 14 to form and capture pleats.
Figure 22B:
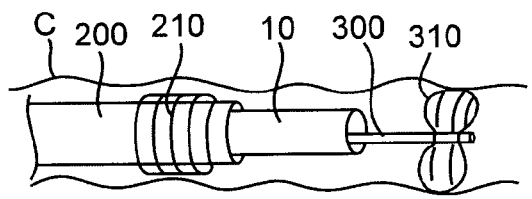
Figure 22C:
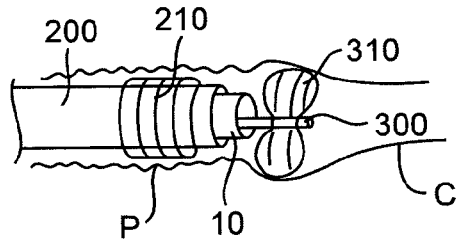
Figure 22D:
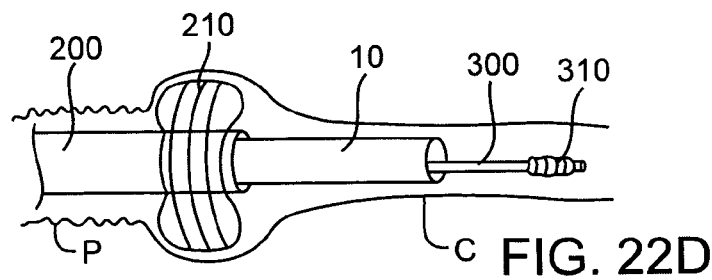

Engagement catheter 300 may be used in conjunction with oversheath pleating apparatus and/or pleat engagement/capture sheaths described previously to induce and/or capture colon pleats. In FIG. 22, a balloon engagement tip embodiment of catheter 300 is used in conjunction with scope 10 and pleat capture sheath 200 of FIG. 14 to pleat colon C. In FIG. 22A, catheter 300 is advanced through working channel 14 of scope 10, such that balloon engagement tip 310 is disposed distal of the scope. Sheath 200 is advanced over scope 10 to a position proximal of the distal end of the scope. Balloon engagement tip 310 of catheter 300 then is activated to engage and anchor against the colon, as in FIG. 22B. In FIG. 22C, catheter 300 is withdrawn relative to scope 10 and sheath 200, thereby pleating the colon. Engagement anchor 210 of pleat capture sheath 200 then is activated to capture pleat P, as seen in FIG. 22D. Catheter 300 then may be de-activated and advanced again to engage a new section of colon C.

Referring now to FIG. 23, an embodiment of the present invention is described comprising multiple external sheaths and anchors. Apparatus 350 comprises a balloon-tipped, Mother-Daughter sheath assembly having mother sheath 352 with balloon 353 and daughter sheath 354 with balloon 355. Sheaths 352 and 354 may be used to "hand over hand" pull the colon proximally, in which each sheath operates similar to the balloon tipped sheath initially described. Providing multiple engagement sheaths facilitates more intricate pleating of the colon.

Figure 23A:
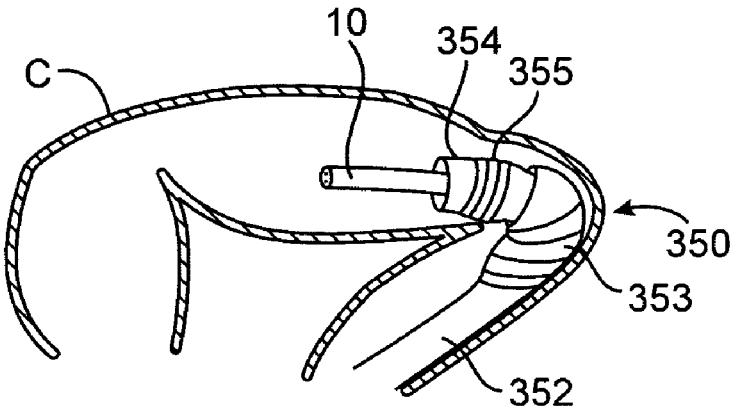
FIGS. 23A-23C are side views, partially in section, illustrating a method of pleating the colon according to the present invention.
Figure 23B:
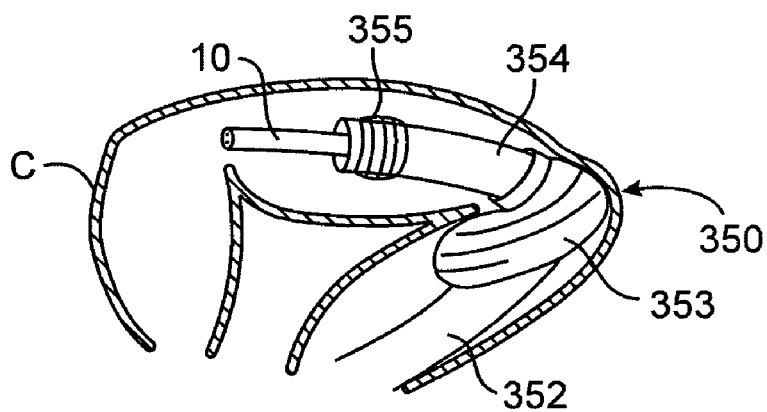
Figure 23C:
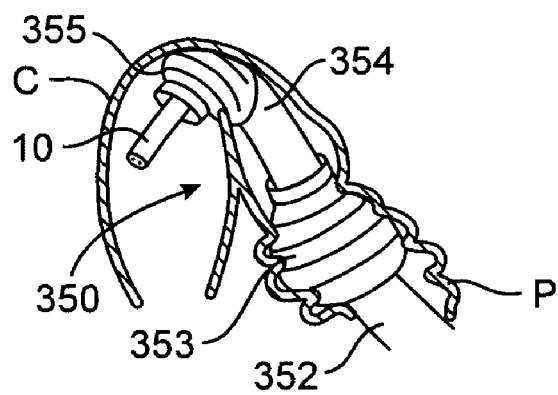

The Mother-Daughter sheath assembly of apparatus 350 may be introduced over scope 10, as seen in FIG. 23A. In FIG. 23B, balloon 353 of mother sheath 352 is activated to anchor colon C to the mother sheath, and daughter sheath 354 is advanced with scope 10. Simultaneously, mother sheath 352 is withdrawn, thereby pleating a portion of the colon. Balloon 355 of daughter sheath 354 then is activated, as seen in FIG. 23C, and the daughter sheath is withdrawn relative to the scope. Immediately after activation of daughter balloon 355, mother balloon 353 is deflated. As daughter sheath 354 completes its withdrawal, a new section of colon C is pleated over deflated mother balloon 355. The mother balloon then is re-inflated, capturing the two sections of colon in a pleat. Daughter balloon 355 then is deflated, and daughter sheath 354 is advanced again into a new section of the colon. This procedure may be repeated as many times as desired, and the sheaths may be advanced and inflated as far as, and as much as, desired.

Such stepwise formation of a pleat alternatively may be achieved in a similar mother-daughter manner using any of the other expanding or suction anchors described previously. Furthermore, the sheaths of apparatus 350 optionally may be moved relative to one another, and/or the balloons inflated and deflated, using a mechanical or electro-mechanical actuator. The actuator may include a handle/slider that is coupled to reciprocating inflation bladders. The arrangement may be actuated by repeatedly engaging a trigger or slide by the user.

With reference now to FIG. 24, a continuous anchor/pleating engagement sheath is described. Apparatus 400 comprises sheath 410 having external thread-like spiral rib 420. The spiral rib may comprise, for example, an elongated balloon that is introduced in a low profile deflated state. Once in a desired position, rib 420 may be activated by inflation, and then used to rotationally draw the colon into a pleat.

Figure 24A:
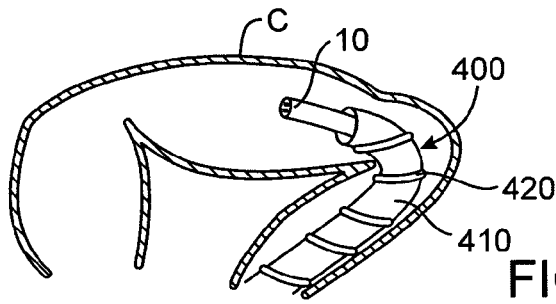
FIGS. 24A-24C are side views, partially in section, illustrating a method of pleating the colon with continuous engagement apparatus of the present invention.
Figure 24B:
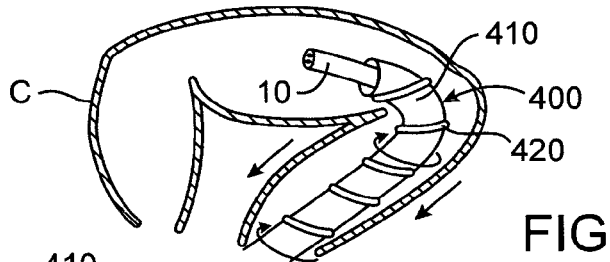
Figure 24C:
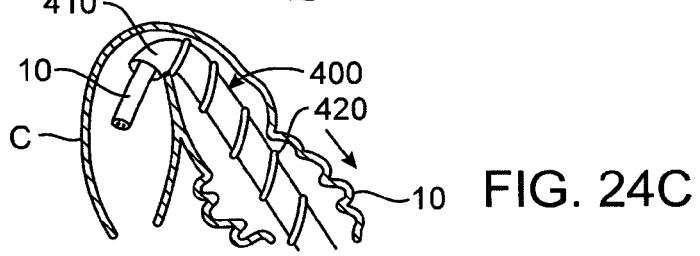

As seen in FIG. 24A, sheath 410 is slid into place over scope 10. In FIG. 24B, a secondary twisting rotation engages colon C along rib 420, which draws the colon down the length of sheath 410 like an auger and pleats the colon, as in FIG. 24C. Colon C alternatively may be pleated by initially screwing apparatus 400 into position, with no linear advancement of sheath 410 over scope 10. The sheath would be positioned slightly in the rectum and rotated to bring the colon down over it. Preferably, a hybrid motion comprising some linear advancement and some twisting would be used to achieve pleating.

Figure 25A:
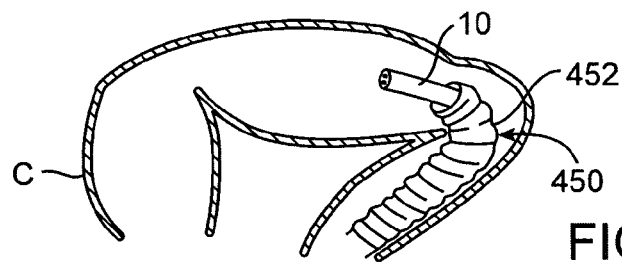
FIGS. 25A-25C are side views, partially in section, illustrating a method of pleating with alternative continuous engagement apparatus comprising a corrugated tube.
Figure 25B:
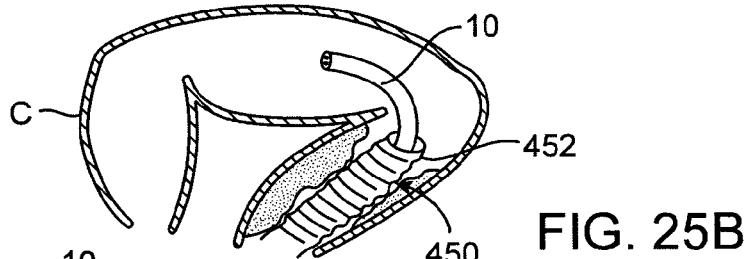
Figure 25C:
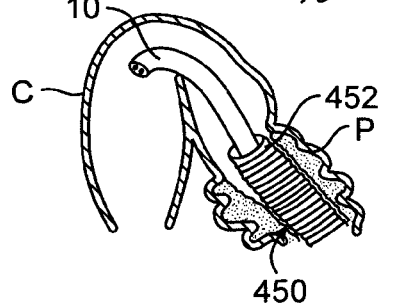

With reference to FIG. 25, another embodiment of a continuous engagement sheath is described comprising an expandable corrugated tube. In FIG. 25A, expandable tube 452 of apparatus 450 is inserted into colon C in its extended collapsed form. Apparatus 450 comprises a thin walled inner sheath (not shown) attached to the distal tip of tube 452. Retracting the inner sheath while holding the outer corrugated tube stationary causes the corrugations to expand outward and engage the colon wall, as in FIG. 25B. Tube 452 may be used to actively engage the mucosa, or the enhanced frictional surface of the compressed corrugations may engage the length of the colon wall. As corrugations form along tube 452 due to withdrawal of the inner sheath, the sheath tip moves proximally, bringing with it the engaged colon, as in FIG. 25C. Apparatus 450 may be further retracted after expansion/corrugation of tube 452 to further pleat the engaged colon.

Figure 26A:
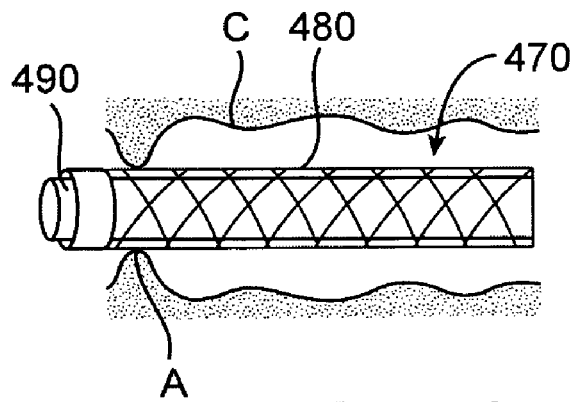
FIGS. 26A and 26B are side views, partially in section, illustrating a method of pleating with braided continuous engagement apparatus.
Figure 26B:
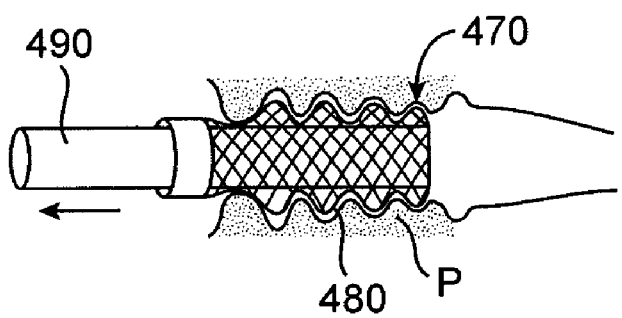

FIG. 26 illustrate yet another embodiment of apparatus of the present invention that continuously engages the colon wall. Apparatus 470 comprises expanding braid tube or sleeve 480 that is disposed over inner sheath 490. As the inner sheath is pulled proximal while the braid sleeve is held at anus A, as in FIG. 26A, the distal tip junction of sleeve 480 and sheath 490 is withdrawn down the colon. This is accompanied by the textured braid sleeve expanding to engage the colon wall. Continued withdrawal of the inner sheath pulls the tip back further and continues braid expansion, thereby engaging and pleating the colon, as in FIG. 26B. Apparatus 470 is similar to apparatus 170 of FIG. 11, as well as apparatus 170' of FIG. 12, except that engagement braid 480 is disposed over a substantially greater longitudinal distance along the apparatus.

Figure 27:
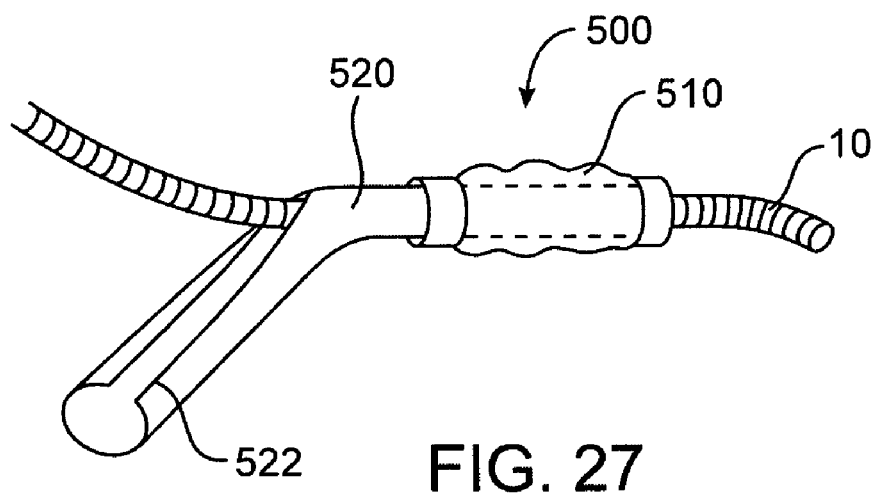
FIG. 27 is an isometric view of continuous engagement apparatus comprising a braided mesh and a split sheath.

With reference to FIG. 27, apparatus 500 comprises braid tube or sleeve 510 coupled at its distal end to inner sheath 520. The inner sheath comprises optional split or seam 522, such that as it is removed from the colon it can be "pealed" away from scope 10. Split 522 may comprise a thinning in the wall of sheath 520 to facilitate tearing thereof, or may comprise a zipper or other similar mechanism to permit the sheath to be reformed even after it has been split. The split sheath is beneficial in that it would not occupy space over the scope's shaft outside of the patient; many colonoscopists value the ability to hold the scope shaft directly near the anus to obtain adequate feel of the scope and optimum scope maneuvering.

Another feature demonstrated by a braid pleating sleeve is its ability to be very flexible in its elongated state. When it is compressed it has a tendency to straighten and feel much firmer. The braid pleating sheath therefore may act as a flexibly placed pleating sheath that transforms into a sturdy, more conventional straightening tube after activation.

Figure 28A:
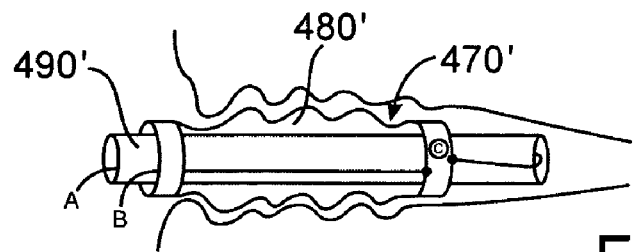
FIGS. 28A and 28B are side views of cable-actuated braided engagement apparatus of the present invention.
Figure 28B:
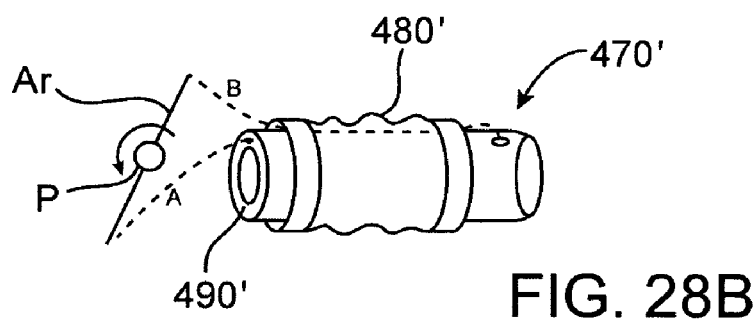

Referring now to FIG. 28, further alternative pleating braid apparatus is described. When pleating with apparatus 470', inner sheath 490' is left in position, and pleating braid 480' is withdrawn or extended by activating opposing cables A and B. Distal bushing C of the pleating braid may be coupled to one or more pleat-forming cables B and one or more return cables A, as seen in FIG. 28A. When cable B is tensioned, distal collar C is drawn in the proximal direction towards the proximal bushing, thereby pleating the braid and inducing the colon to pleat. When cable A is tensioned and cable B is released, distal bushing C may be pulled in the distal direction to return the braid to its elongated, non-pleated state. To reciprocate tension between cables A and B, lever arm Ar having pivot P may be coupled to the cables. As illustrated in FIG. 28B, when a user turns the lever arm in the counter-clockwise direction, cable B is tensioned, taking up slack within cable A. Similarly, when the lever arm is turned in the clockwise direction, cable A is tensioned, and slack within cable B is taken up.

Figure 29A:
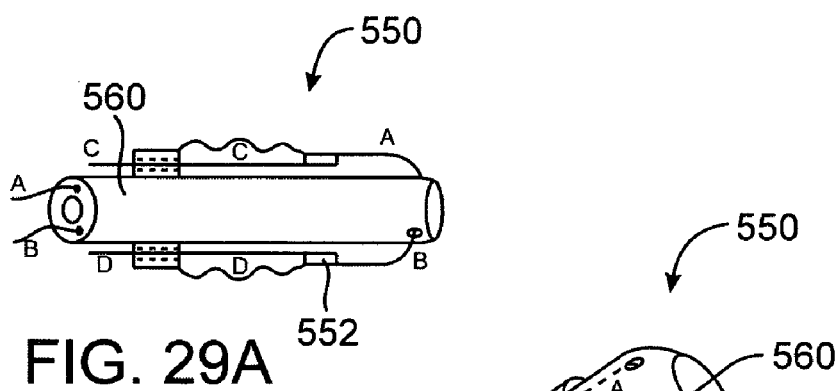
FIGS. 29A and 29B are, respectively, a side view, partially in section, and an isometric view of an alternative embodiment of the apparatus of FIG. 28.
Figure 29B:
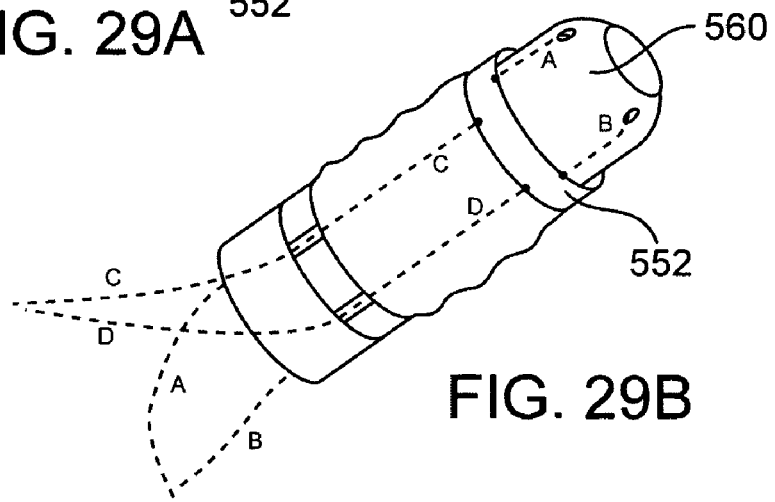

With reference to FIG. 29, an alternative cable-controlled pleating sleeve is shown. Apparatus 550 comprises pleat-forming cables C and D, which extend from distal slide collar 552, through proximal fixed collar 554 and out of the patient. Apparatus 550 further comprises return cables A and B, which extend from distal slide collar 552 through sheath 560 and out of the patient. It may be preferential to have this arrangement mirrored to better balance the cable forces. For clarity of the sketch, mirrored cables are not shown in FIG. 29.

Although preferred illustrative embodiments of the present invention are described above, it will be evident to one skilled in the art that various changes and modifications may be made therein without departing from the invention. For example, although the apparatus has been described as suited for pleating the colon, it should be understood that the apparatus alternatively may be used to pleat any other suitable body lumen, for example, alternative portions of the gastrointestinal lumen, the small bowel, vascular lumens, etc. It is intended in the appended claims to cover all such changes and modifications that fall within the true spirit and scope of the invention.

What is claimed is:

1. A method for advancing an endoscope through a body lumen, comprising:
   advancing an endoscope having a steerable distal end and a flexible conduit through the body lumen;
   engaging a region of body lumen distal to the flexible conduit via the steerable distal end;
   retracting the endoscope relative to the flexible conduit such that a portion of the body lumen is retracted relative to the flexible conduit;
   rigidizing the flexible conduit;
   disengaging the steerable distal end from the region of body lumen; and
   advancing the endoscope relative to the rigidized flexible conduit.

2. The method of claim 1 wherein advancing an endoscope comprises advancing through a bowel of a patient.

3. The method of claim 1 wherein engaging a region of body lumen comprises temporarily anchoring the steerable distal end to the region of body lumen.

4. The method of claim 1 wherein engaging a region of body lumen comprises hooking the steerable distal end to the region of body lumen.

5. The method of claim 1 wherein retracting the endoscope comprises proximally withdrawing the endoscope while maintaining the engaged region of body lumen to the steerable distal end.

6. The method of claim 1 wherein retracting the endoscope further comprises straightening the portion of the body lumen.

7. The method of claim 1 wherein disengaging the steerable distal end comprises releasing the steerable distal end from the region of body lumen.

* * * * *